US011951466B2

United States Patent
Franke et al.

(10) Patent No.: US 11,951,466 B2
(45) Date of Patent: Apr. 9, 2024

(54) PROCESS FOR REGENERATING A CATALYST FOR THE HYDROFORMYLATION OF OLEFINS IN THE GAS PHASE

(71) Applicant: Evonik Oxeno GmbH & Co. KG, Marl (DE)

(72) Inventors: Robert Franke, Marl (DE); Linda Arsenjuk, Dortmund (DE); Jessika Schüller, Gunderath (DE); Frank Stenger, Alzenau (DE); Vinzenz Fleischer, Marl (DE); Marc Oliver Kristen, Haltern am See (DE)

(73) Assignee: EVONIK OXENO GMBH & CO. KG, Marl (DE)

( * ) Notice: Subject to any disclaimer, the term of this patent is extended or adjusted under 35 U.S.C. 154(b) by 56 days.

(21) Appl. No.: 17/716,170

(22) Filed: Apr. 8, 2022

(65) Prior Publication Data

US 2022/0379294 A1 Dec. 1, 2022

(30) Foreign Application Priority Data

May 18, 2021 (EP) ..................................... 21174300

(51) Int. Cl.
 *B01J 31/16* (2006.01)
 *B01J 31/40* (2006.01)
 *B01J 38/50* (2006.01)

(52) U.S. Cl.
 CPC .................................... *B01J 38/50* (2013.01)

(58) Field of Classification Search
 CPC ............. B01J 31/1616; B01J 2231/321; B01J 31/4053
 See application file for complete search history.

(56) References Cited

U.S. PATENT DOCUMENTS

| 9,206,105 | B2 | 12/2015 | Christiansen et al. |
| 9,272,973 | B2 | 3/2016 | Fridag et al. |
| 9,409,844 | B2 | 8/2016 | Christiansen et al. |
| 9,499,463 | B2 | 11/2016 | Christiansen et al. |
| 9,556,096 | B2 | 1/2017 | Christiansen et al. |
| 10,501,392 | B2 | 12/2019 | Fridag et al. |
| 10,526,356 | B2 | 1/2020 | Dyballa et al. |
| 10,633,302 | B2 | 4/2020 | Nadolny et al. |
| 10,647,650 | B2 | 5/2020 | Hecht et al. |
| 10,654,784 | B2 | 5/2020 | Hasselberg et al. |
| 10,850,261 | B2 | 12/2020 | Nadolny et al. |
| 10,882,027 | B2 | 1/2021 | Nadolny et al. |
| 11,008,275 | B2 | 5/2021 | Kucmierczyk et al. |
| 11,253,844 | B2 | 2/2022 | Nadolny et al. |
| 2013/0317246 | A1 | 11/2013 | Kreidler et al. |
| 2020/0302064 | A1 | 12/2020 | Kucmierczyk et al. |
| 2020/0391194 | A1 | 12/2020 | Kucmierczyk et al. |
| 2020/0392057 | A1 | 12/2020 | Kucmierczyk et al. |
| 2021/0179534 | A1 | 6/2021 | Schulz et al. |
| 2021/0340091 | A1 | 11/2021 | Hasselberg et al. |
| 2022/0033337 | A1 | 2/2022 | Brächer et al. |

FOREIGN PATENT DOCUMENTS

| DE | 10 2011 002 640 A1 | 7/2012 |
| EP | 3 318 569 A1 | 5/2018 |
| EP | 3 532 886 A1 | 9/2019 |
| EP | 3 632 885 A1 | 4/2020 |
| EP | 3 632 887 A1 | 4/2020 |
| EP | 3 632 888 A1 | 4/2020 |
| EP | 3 632 889 A1 | 4/2020 |
| EP | 3 736 258 A1 | 11/2020 |
| EP | 3 744 707 A1 | 12/2020 |
| WO | 2014/056733 A1 | 4/2014 |
| WO | 2015/028284 A1 | 3/2015 |
| WO | 2018/078417 A1 | 5/2018 |
| WO | 2020/070052 A1 | 4/2020 |

OTHER PUBLICATIONS

Gluth et al., U.S. Appl. No. 17/549,709, filed Dec. 13, 2021.
Quell et al., U.S. Appl. No. 17/549,256, filed Dec. 13, 2021.

*Primary Examiner* — Catherine S Branch

(74) *Attorney, Agent, or Firm* — Grüneberg and Myers PLLC

(57) ABSTRACT

The present invention relates to a simple process for regenerating a hydroformylation catalyst consisting of a heterogenized catalyst system on a support consisting of a porous ceramic material. The invention also relates to a process for the start-up of the hydroformylation reaction after regeneration according to the invention.

20 Claims, No Drawings

PROCESS FOR REGENERATING A CATALYST FOR THE HYDROFORMYLATION OF OLEFINS IN THE GAS PHASE

CROSS REFERENCE TO RELATED APPLICATIONS

This application is a 35 U.S.C. § 119 patent application which claims the benefit of European Application No. 21174300.0 filed May 18, 2021, which is incorporated herein by reference in its entirety.

FIELD

The project, which resulted in this patent application, was financed in the scope of grant No. 869896 of the Horizon 2020 research and innovation program of the European Union.

The invention relates to a simple process for regenerating a hydroformylation catalyst consisting of a heterogenized catalyst system on a support composed of a porous ceramic material. The invention also relates to a process for the start-up of the hydroformylation reaction after regeneration according to the invention.

BACKGROUND

Hydroformylation is one of the most important reactions in industrial scale chemistry, having an annual global production capacity of several million tonnes. This involves reacting alkenes (olefins) with a mixture of carbon monoxide and hydrogen (also: synthesis gas or syngas) using a catalyst to give aldehydes, which are important and valuable intermediates in the production of chemical bulk products such as alcohols, esters or plasticizers.

Hydroformylation is conducted exclusively under homogeneous catalysis on the industrial scale. The soluble transition metal catalyst systems are typically based on cobalt or rhodium, which is often used together with phosphorus-containing ligands, for example phosphines or phosphites, for the hydroformylation of comparatively short-chain olefins.

There are various problems in the known processes, and these are especially linked to the fact that both rhodium and cobalt and compounds thereof are comparatively costly. There is a high level of energy expenditure and complex chemical engineering in order to very substantially avoid losses of catalyst during the hydroformylation process, for example by catalyst recycling steps, some of them very complex. Moreover, product purification steps are becoming more complex in order to ensure that as far as possible no catalyst residues remain in the product.

Further problems with the known homogeneously catalyzed processes are the stability of the ligands, which have to withstand the hydroformylation conditions, such as temperature, pressure, pH etc., and consumption of the solvent used during the process, which must be compensated for by replenishment.

In order to get round the aforementioned problems in the homogeneously catalyzed hydroformylation, there has been development of hydroformylation processes in which the catalyst system is heterogenized, especially by immobilization on a support material (cf. introductory discussion in WO 2015/028284 A1). Heterogenized systems on monoliths have also recently been developed, for example in patent applications EP 3 632 885 A1, EP 3 744 707 A1, EP 3 532 886 A1, EP 3 736 258 A1, EP 3 632 888 A1, EP 3 632 887 A1 or EP 3 632 889 A1. The terms "heterogenization" and "immobilization" should accordingly be understood such that the catalyst is immobilized by formation of a thin liquid film with the aid of an ionic liquid on the surface and/or in the pores of a solid support material and there is no reaction solution in the conventional sense in which the catalyst is homogeneously dissolved.

However, the problem with the immobilized or heterogenized systems mentioned above is that, after a certain service life, decreasing catalyst activity and hence a reduction in conversion and selectivity can be observed. This may be attributable to various effects, for example condensation of the products in the pores and corresponding further reactions such as aldol condensations, or the formation of water that can lead to deactivation of the ligands, the formation of by-products and/or the flooding of the pores, as a result of which the catalyst may be discharged.

SUMMARY

The object of the present invention, therefore, consists of providing a simple process for regenerating hydroformylation catalysts consisting of a heterogenized catalyst system on a support composed of a porous ceramic material.

DETAILED DESCRIPTION

The object is achieved by the process according to the invention. Here, the catalyst in a vessel is brought into contact with a solution of a solvent and a phosphorus-containing ligand. The present invention therefore relates to a process for regenerating a hydroformylation catalyst consisting of a heterogenized catalyst system, in a vessel,
  wherein the catalyst system comprises a metal of Group 8 or 9 of the Periodic Table of the Elements and at least one organic phosphorus-containing ligand and is present heterogenized on a support, wherein the support consists of a porous ceramic material and is in the form of granules or in the form of a monolith,
  wherein the process comprises at least the following steps:
  a) filling the vessel with a solution consisting of the phosphorus-containing ligand and a solvent, and allowing it to stand for at least one hour,
  b) discharging the solution from the vessel.

The advantage of the process according to the invention is that it can be achieved very simply and cost-effectively. In contrast to known processes, the solution for the regeneration must comprise the ligand, but not the metal from Group 8 or 9 of the Periodic Table of the Elements. The preparation of the solution is therefore less costly. Since the metals suitable for the catalyst system are also quite expensive, these costs may be saved in the process according to the invention.

According to the process according to the invention, it is possible, surprisingly, to regenerate the hydroformylation catalyst in which said catalyst is left to stand for at least one hour in a solution consisting of the phosphorus-containing ligand and a solvent. In a preferred embodiment of the present invention, the hydroformylation catalyst is left to stand in the solution for at least 12 hours, particularly preferably for at least 24 hours. In principle, the hydroformylation catalyst may be left to stand in the solution for a quite longer period. However, due to the fact that the catalyst should be used again in the production as quickly as possible, it makes sense for the catalyst to be left to stand in the solution for not more than 72 hours.

The vessel, in which the hydroformylation catalyst is located, may in principle be any type of vessel. However, the vessel is preferably a closed vessel having at least one inlet and one outlet. The vessel is particularly preferably a reactor in which a hydroformylation may be carried out using the hydroformylation catalyst. In a particularly preferred embodiment of the present invention, the process is carried out in situ in the reactor in which the hydroformylation catalyst was already present during the preceding hydroformylation. As a result, the hydroformylation catalyst may remain in the reactor and does not have to first be removed and be filled into another vessel. Nevertheless, it may be advantageous for plant or process technology reasons if the catalyst is removed and is regenerated in another vessel, the regeneration thus taking place ex situ.

In the case of in situ regeneration, it may be advantageous if two or more, i.e. at least two parallel reactors are present. A so-called swing cycle can then be carried out. This means that at least one of the reactors is in operation and in which the desired hydroformylation is being carried out, while at least one other reactor is being regenerated. As soon as the regeneration is completed, the respective reactor may also be put into operation or be kept in standby until deployed.

Before the regeneration is carried out, no matter whether it is carried out in situ or ex situ, the reactant streams of the hydroformylation, i.e. the substance to be hydroformylated and the synthesis gas, are firstly shut off. The reactor in which the hydroformylation catalyst is still located can then be flushed with an inert gas. As a result, residues of the reactants may be expelled. The reactor is also inertized by the removal of reactants. It is further preferred that the volume flow rate per hour of the inert gas used during flushing is 1-fold to 100-fold of the volume of the vessel or of the reactor. All known inert gases are suitable as inert gases for flushing. The inert gas is preferably selected from the group consisting of nitrogen, helium, neon, $CO_2$ and argon. Particular preference is given to nitrogen as inert gas. If the reactor is flushed, it is preferable that the reactor cools to ambient temperature during flushing.

In the first step of the process according to the invention (step a)), the vessel in which the hydroformylation catalyst is then located (in situ or ex situ) is filled with the solution for the regeneration. The filling is preferably carried out at room temperature (20 to 25° C.) and standard pressure (ca. 1 bar). Furthermore, the filling is preferably carried out under an inert gas atmosphere, especially in a previously inertized vessel or reactor. All known inert gases are suitable as inert gases for the filling. The inert gas is preferably selected from the group consisting of nitrogen, helium, neon, $CO_2$ and argon. Particular preference is given to nitrogen as inert gas.

After the hydroformylation catalyst has been left to stand in the vessel or reactor (ex situ or in situ) for at least one hour, preferably for at least 12 hours, particularly preferably for at least 24 hours, the solution is discharged from the vessel or reactor in step b). This can be achieved either by means of a suitable apparatus, for example a pump, or effected without an apparatus of this kind, i.e. hydrostatically. The solution in step b) is preferably discharged hydrostatically.

It may be the case that after discharging the solution from the vessel or the reactor in step b) of the process according to the invention, solvent residues are still present. In order to remove solvent residues or to prevent that solvent residues remain behind in the vessel or reactor, the temperature can be increased and/or the pressure can be reduced in the vessel or reactor, during the discharge in step b) or after discharging the solution, in order to evaporate solvent still present. In an alternative embodiment of the present invention, the solvent is the reaction product of the preceding hydroformylation, i.e. in this case the resulting aldehyde. In such a case, it is sufficient if the solvent is discharged. An additional evaporation is then not absolutely necessary.

If during the discharge in step b) or after discharging the solution the temperature is increased and/or the pressure is reduced in the vessel or reactor, the exact values for temperature and pressure are variable in wide ranges. In this case, the solvent and the boiling point thereof depend on the pressure. Ultimately, substances boil at a lower temperature if the pressure is lower. In this respect, the designation of specific temperatures is difficult. In a preferred embodiment, the temperature in step b) is increased to at least 80° C., preferably at least 90° C. It is further preferred that, when increasing the temperature and/or when reducing the pressure, the reactor is flushed with an inert gas. All known inert gases are suitable as inert gases for this purpose. The inert gas is preferably selected from the group consisting of nitrogen, helium, neon, $CO_2$ and argon. Particular preference is given to nitrogen as inert gas. It is further preferred that the inert gases are identical for the flushing, the filling (step a) and the discharging (step b) in order to reduce the preparative effort.

The solution which is used for the regeneration consists in accordance with the invention of the phosphorus-containing ligand of the hydroformylation catalyst used and a solvent. All substances which are capable of dissolving the phosphorus-containing ligand are suitable as solvent. Suitable as solvents are, for example, dichloromethane, THF, pentanol, propanal, propanol or pentanal. The concentration of the organic phosphorus-containing ligand may be varied depending on the solubility limit of the selected solvent. The concentration of the organic phosphorus-containing ligand is preferably between 1 and 70 g/L, preferably between 5 and 40 g/L.

The organic phosphorus-containing ligand of the catalyst system according to the invention can be any ligand suitable for the hydroformylation. Appropriate ligands are described in the specialist literature and are known to those skilled in the art. The organic phosphorus-containing ligand preferably has the general formula (I)

$$R'\text{-}A\text{-}R''\text{-}A\text{-}R''' \qquad (I)$$

where R', R" and R'" are each organic radicals, with the proviso that R' and R'" are non-identical, and both A are each a bridging —O—P(—O)$_2$ group, wherein two of the three oxygen atoms —O— are each attached to the radical R' and to the radical R'". The organic radicals R', R" and R'" preferably do not comprise any terminal trialkoxysilane groups.

In a preferred embodiment, R', R" and R'" in the compound of the formula (I) are preferably selected from substituted or unsubstituted 1,1'-biphenyl, 1,1'-binaphthyl and ortho-phenyl groups, especially from substituted or unsubstituted 1,1'-biphenyl groups, with the proviso that R' and R'" are non-identical. Particularly preferably, the substituted 1,1'-biphenyl groups have an alkyl group and/or an alkoxy group in the 3,3' and/or 5,5' positions of the 1,1'-biphenyl base skeleton, especially a C1-C4 alkyl group, particularly preferably a tert-butyl and/or methyl group, and/or preferably a C1-C5 alkoxy group, particularly preferably a methoxy group. Examples of appropriate compounds is the ligand biphephos, which is described for example in DE 10 2011 002 640 A1, or ligands described in WO 2014/056733 A1 or EP 3 318 569 A1.

The catalyst system according to the invention further comprises a metal from Group 8 or 9 of the Periodic Table of the Elements. Typical metals for hydroformylation are known to those skilled in the art. The metal from Group 8 or 9 of the Periodic Table of the Elements is preferably selected from the group consisting of iron, ruthenium, iridium, ruthenium, cobalt or rhodium. Particular preference is given to cobalt and rhodium.

According to the invention, the aforementioned catalyst system is in heterogenized form on a support of a porous ceramic material. In the context of the present invention, the expression "heterogenized on a support" is understood to mean that the catalyst system is immobilized via formation of a thin, solid or liquid film with the aid of a stabilizer and/or, optionally, of the ionic liquid on the inner and/or outer surface of a solid support material. The film may also be solid at room temperature and liquid under reaction conditions.

The porous support material is preferably selected from the group consisting of a nitridic ceramic, a carbidic ceramic, a silicidic ceramic and mixtures thereof, for example carbonitridic materials.

The nitridic ceramic is preferably selected from silicon nitride, boron nitride, aluminium nitride and mixtures thereof. The carbidic ceramic is preferably selected from silicon carbide, boron carbide, tungsten carbide or mixtures thereof. Also conceivable are mixtures of carbidic and nitridic ceramic, called the carbonitrides. The silicidic ceramic is preferably molybdenum silicide. The support according to the present invention to which the catalyst system is applied preferably consists of a carbidic ceramic, particularly preferably of silicon carbide.

According to the invention, the support is present either in the form of a monolith or in the form of granules. If the support is present in the form of a monolith, the term "monolith" is understood to mean that the support consists of a block of the ceramic material, i.e. is a three-dimensional object. The block may either be in one-piece form or consist of multiple, i.e. at least two, individual parts that may be joined together to form the block and/or are joined to one another in a fixed or partable manner.

If the support is present in the form of granules, the support consists of small particles. The size of the particles is variable and depends, for example, on the reaction regime. In the case of rapid reactions, rather small particles are suitable, whereas in the case of reactions that proceed slowly, larger particles may also be used. It is preferable that the average particle diameter (d50) of the support, if it is present in the form of granules, is in the range of 0.01 mm to 70 mm, preferably 0.03 to 60 mm, particularly preferably of 0.05 mm to 50 mm. The average particle diameter may be determined by imaging methods, and may be determined in particular by the methods cited in the standards ISO 13322-1 (Dec. 1, 2004 version) and ISO 13322-2 (Nov. 1, 2006 version). The granules may be prepared by methods known to those skilled in the art. For example, this may be effected by mechanically comminuting a monolith composed of the carbidic, nitridic, silicidic material or mixtures thereof, for example using a jaw crusher, and adjusting the particle size of the resulting crushed granules by means of sieving.

In addition, the support, irrespective of whether it is in the form of a monolith or in the form of granules, is porous, i.e. the support has pores. The pore diameter is preferably in the range from 0.9 nm to 30 µm, preferably in the range from 10 nm to 25 µm and particularly preferably in the range from 70 nm to 20 µm. Pore diameter can be determined by means of nitrogen adsorption or mercury porosimetry in accordance with DIN 66133 (1993-06 version). In a preferred embodiment, the support comprises at least some continuous pores extending from one surface to another surface. It is also possible that multiple pores are connected to one another and hence overall form a single continuous pore.

The production of the support from a porous ceramic material on which the catalyst system is in heterogenized form is effected as described below: a so-called washcoat is in addition applied to the support provided composed of the ceramic material, which washcoat, based on the ceramic material of the support, is composed of the same or a different ceramic material, preferably silicon oxide. The washcoat itself may be porous or non-porous, preference being given to the washcoat being non-porous. The particle size of the washcoat is preferably 5 nm to 3 µm, preferably 7 nm to 700 nm. The washcoat is used to introduce or to generate the desired pore size and/or to increase the surface area of the support. The washcoat can especially be applied by means of dipping (dip-coating) into a washcoat solution containing the ceramic material of the washcoat, possibly also as a precursor. The amount of washcoat on the support is ≤20% by weight, preferably ≤15% by weight, particularly preferably ≤10% by weight, based on the total amount of the support.

Subsequently, the catalyst system may be applied, for example by impregnation, as has been described in patent applications EP 3 632 885 A1 or WO 2020/070052 Q1.

The catalyst system may comprise further substances in addition to the ligand and the metal. The advantage of the regeneration process according to the invention is that the regeneration solution does not have to comprise any of the substances specified below. It is preferred in accordance with the invention that the catalyst system additionally comprises a stabilizer. The stabilizer for the catalyst system according to the invention is preferably an organic amine compound, particularly preferably an organic amine compound comprising at least one 2,2,6,6-tetramethylpiperidine unit according to formula (II):

(II)

In a particularly preferred embodiment of the present invention, the stabilizer is selected from the group consisting of the compounds of the following formulae (II.1), (II.2), (II.3), (II.4), (11.5), (II.6), (II.7) and (II.8).

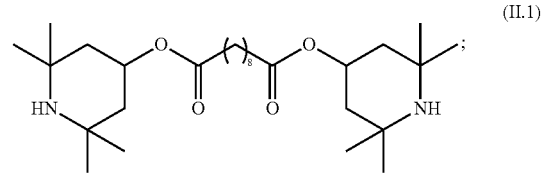
(II.1)

(II.2)

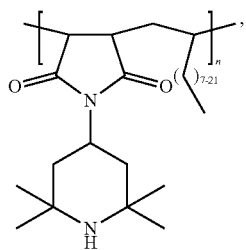

where n is an integer from 1 to 20;

(II.3)

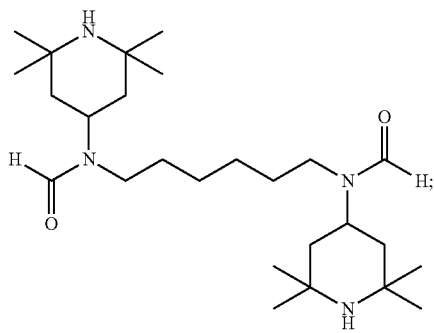

(II.4)

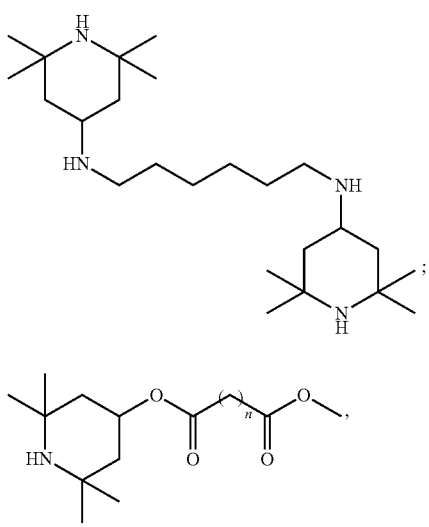

(II.5)

where n is an integer from 1 to 12:

(II.6)

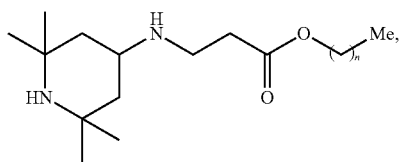

where n is an integer from 1 to 17;

(II.7)

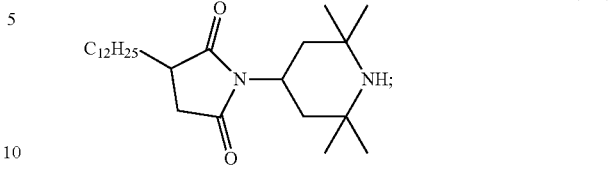

(II.8)

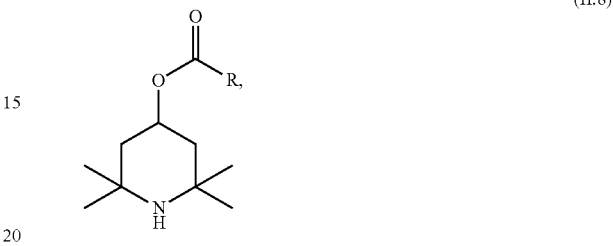

where R is a C6- to C20-alkyl group.

The catalyst system may also comprise an ionic liquid. However, it is preferable if the catalyst system does not comprise any ionic liquid.

When the regeneration process is complete, the reaction, i.e. the hydroformylation, can be restarted. If the regeneration has been carried out ex situ, the catalyst system firstly of course has to be filled into the hydroformylation reactor. In the case of an in situ regeneration, the catalyst system is already present therein. After the regeneration, the reactor and the reaction are started up. The relevant process is characterized in that a gaseous feedstock mixture comprising C2- to C8-olefins to be hydroformylated together with a synthesis gas mixture is introduced into the reactor, and the composition of the feedstock mixture and/or the composition of the synthesis gas mixture is varied in two or more steps at a constant volume flow rate in that the proportion of C2- to C8-olefins to be hydroformylated in the feedstock mixture and/or the proportion of synthesis gas in the synthesis gas mixture is increased in a stepwise manner, with the proviso that a maximum conversion of the C2- to C8-olefins used of 40 to 90% during the entire start-up is not exceeded.

Using this process, a mild activation and alleviation of the maximum starting activity of the hydroformylation catalyst can be achieved. This results in an extended service life of the catalyst, and also in partial or complete prevention of liquid phase formation, which may result in deactivation or washing out of the catalyst system.

The feedstock mixture used for the process according to the invention may be any mixture comprising C2- to C8-olefins, preferably C2- to C5-olefins, especially ethene, propene, 1-butene, 2-butene, isobutene, 1-pentene or 2-pentene, as reactants. The amount of olefins in the feed mixtures should naturally be high enough to be able to economically conduct a hydroformylation reaction. This especially includes technical mixtures from the petrochemical industry, for example raffinate streams (raffinate I, II or III) or crude butane. Crude butane according to the present invention comprises 5 to 40% by weight butenes, preferably 20 to 40% by weight butenes (the butenes are composed of 1 to 20% by weight 1-butene and 80 to 99% by weight 2-butene) and 60 to 95% by weight butanes, preferably 60 to 80% by weight butanes.

The synthesis gas mixture according to the present invention consists of synthesis gas for hydroformylation, i.e. comprising hydrogen and carbon monoxide, preferably in a molar ratio of 60:40 to 40:60, more particularly 50:50, and optionally small amounts of impurities. The synthesis gas can be produced and provided by known processes.

In the start-up procedure, it is provided that either the proportion of synthesis gas in the synthesis gas mixture or the proportion of olefins in the feedstock mixture are varied by stepwise increases. The proportions of synthesis gas and olefins to each other may also additionally be varied, wherein the number of steps in the increase of the proportions may also be different from each other. At the start, the proportion of the synthesis gas and/or the proportion of olefins should be lower than commonly used in hydroformylation and which are then successively increased until, after full start-up and transition to hydroformylation, the final composition(s) has been attained.

The proportion of olefins in the feedstock mixture and/or the proportion of synthesis gas in the synthesis gas mixture is increased in two or more steps, i.e. in at least two steps. In a preferred embodiment, the proportion of olefins in the feedstock mixture and/or the proportion of synthesis gas in the synthesis gas mixture is increased in at least three steps, particularly preferably in at least 4 steps.

In order to be able to achieve variation of the proportion of olefins in the feedstock mixture and/or of the proportion of synthesis gas in the synthesis gas mixture, initially an inert gas may be added to the feedstock mixture and/or to the synthesis gas mixture, in order to dilute the feedstock mixture and/or the synthesis gas mixture.

In the first step, preferably as much inert gas is added to the feedstock mixture and/or to the synthesis gas mixture such that the proportion of inert gas in the feedstock mixture and/or in the synthesis gas mixture is in the range of 70% to 90%. The proportion of inert gas in the feedstock mixture and/or in the synthesis gas mixture is then successively reduced in the following step or in the following steps. In the last step of the start-up, the proportion of inert gas in the feedstock mixture and/or in the synthesis gas mixture is then only 10% to 30%. All known inert gases are suitable as inert gases for this purpose. The inert gas is preferably selected from the group consisting of nitrogen, helium, neon, $CO_2$ and argon. Particular preference is given to nitrogen as inert gas.

After the last step, the addition of inert gas is completely stopped. The feedstock mixture and/or synthesis gas mixture are then no longer diluted, but rather are used at their normal, undiluted composition. As a result, the start-up procedure is terminated and the reactor is again in normal operating mode.

Example

A hydroformylation catalyst consisting of a heterogenized catalyst system (Rh, biphephos, bis(2,2,6,6-tetramethyl-4-piperidyl) sebacate (stabilizer) on a support composed of SiC, support as crushed granules having particle size of 3 mm (average fraction size)) was initially charged in a tubular reactor. For the hydroformylation, the reactor was flushed continuously with a gaseous C4-feed (raffinate III) and synthesis gas. The hydroformylation was carried out at a pressure of 10 bar and a temperature of 130° C. During the reaction, the n/iso selectivity of the aldehyde produced was determined (online GC at the reactor outlet for measuring the product composition). It could be established that the n/iso selectivity decreases with time. After ca. 750 hours, the reaction was stopped and regeneration was carried out.

The procedure during the regeneration was as follows:
stop the reactant streams;
flushing the support with nitrogen while cooling the plant to room temperature;
flooding the reactor internal space and support with ligand solution (composition of ligand solution: biphephos in dichloromethane (ca. 67 g/L));
keeping the solution in the reactor for ca. 48 hours;
discharging the solution;
flushing the reactor with nitrogen (ca. 5 g/h) and increasing the temperature to 120° C.;
start-up of the plant (in stages, C4 feed in each case diluted with N2 as described in EP 3 362 887 A1).

After the start-up, the plant was again in normal operating mode, i.e. under the aforementioned hydroformylation conditions which were also present prior to the regeneration. The n/iso selectivity compared with the value prior to the regeneration could be fully restored (see Table 1 below):

TABLE 1

| Selectivities of the reaction investigated | |
|---|---|
| Selectivity at start of experiment | 95% |
| N/iso selectivity prior to treatment with ligand solution (Raff III, 10 bar, 130° C.) | 72% |
| N/iso selectivity after treatment with ligand solution (Raff III, 10 bar, 130° C.) | 96% |

The invention claimed is:

1. A process for regenerating a hydroformylation catalyst consisting of a heterogenized catalyst system, in a vessel,
wherein the catalyst system comprises a metal of Group 8 or 9 of the Periodic Table of the Elements and at least one organic phosphorus-containing ligand and is present heterogenized on a support, wherein the support consists of a porous ceramic material and is in the form of granules or in the form of a monolith,
wherein the process comprises at least the following steps:
a) filling the vessel with a solution consisting of the phosphorus-containing ligand and a solvent, and allowing it to stand for at least one hour, and
b) discharging the solution from the vessel.

2. The process according to claim 1, wherein the solution in the reactor in step a) is kept for at least 12 hours.

3. The process according to claim 1,
wherein the process is carried out in situ in the reactor in which the hydroformylation catalyst is present.

4. The process according to claim 1, wherein the solvent of the solution is dichloromethane, THF, pentanol, propanal, propanol or pentanal.

5. The process according to claim 1, wherein the solution in step b) is discharged hydrostatically.

6. The process according to claim 1, wherein step a) is carried out at ambient temperature.

7. The process according to claim 1, further comprising:
raising the temperature in step b) and flushing the reactor with an inert gas when raising the temperature in step b).

8. The process according to claim 7, wherein the inert gas is nitrogen, helium, neon, $CO_2$ or argon.

9. The process according to claim 1, wherein the support consists of a porous ceramic material which is selected from the group consisting of a silicate ceramic, an oxidic ceramic, a nitridic ceramic, a carbidic ceramic, a silicidic ceramic and mixtures thereof.

10. The process according to claim 1, wherein a washcoat is applied to the support which is composed of the same or another ceramic material.

11. The process according to claim 10, wherein the amount of washcoat on the support is ≤20% by weight, based on the total amount of the support.

12. The process according to claim 1, wherein the organic phosphorus-containing ligand of the catalyst system has the general formula (I)

  (I)

where R', R" and R'" are each organic radicals, with the proviso that R' and R'" are non-identical, and both A are each a bridging —O—P(—O)$_2$ group, wherein two of the three oxygen atoms —O— are each attached to the radical R' and to the radical R'".

13. The process according to claim 1, wherein the catalyst system additionally comprises a stabilizer.

14. The process according to claim 1, wherein the reactor is started up after regeneration of the hydroformylation catalyst, wherein the process is characterized in that
 a gaseous feedstock mixture comprising C2- to C8-olefins to be hydroformylated together with a synthesis gas mixture is introduced into the reactor, and
 the composition of the feedstock mixture and/or the composition of the synthesis gas mixture is varied in two or more steps at a constant volume flow rate in that the proportion of C2- to C8-olefins to be hydroformylated in the feedstock mixture and/or the proportion of synthesis gas in the synthesis gas mixture is increased in a stepwise manner,
 wherein a maximum conversion of the C2- to C8-olefins used of 40 to 90% during the entire start-up is not exceeded.

15. The process according to claim 14, wherein an inert gas is added to the feedstock mixture and/or to the synthesis gas mixture to reduce the proportion of C2- to C8-olefins and/or to reduce the proportion of synthesis gas and the addition of the inert gas is reduced in a stepwise manner corresponding to the stepwise increase of the proportion of C2- to C8-olefins and/or of the proportion of synthesis gas.

16. The process according to claim 1, wherein the solution in the reactor in step a) is kept for at least 24 hours.

17. The process according to claim 2, wherein the process is carried out in situ in the reactor in which the hydroformylation catalyst is present.

18. The process according to claim 2, wherein the solvent of the solution is dichloromethane, THF, pentanol, propanal, propanol or pentanal.

19. The process according to claim 2, wherein the solution in step b) is discharged hydrostatically.

20. The process according to claim 2, wherein step a) is carried out at ambient temperature.

* * * * *